United States Patent [19]

Tamura et al.

[11] 4,252,129
[45] Feb. 24, 1981

[54] DEVICE FOR MEASURING MOTION OF LIVING BODY ORGANS

[76] Inventors: Kohji Tamura, No. 5239, Nibancho, Asahimachi-dori, Niigata-shi, Niigata-ken; Yoshiaki Saitoh, No. 191, Yokomachi, Itoigawa-shi, Niigata-ken, both of Japan

[21] Appl. No.: 958,406

[22] Filed: Nov. 7, 1978

[30] Foreign Application Priority Data
Nov. 10, 1977 [JP] Japan .................... 52-135448

[51] Int. Cl.³ .............................................. A61B 5/10
[52] U.S. Cl. .................................... 128/693; 128/782; 128/903
[58] Field of Search ................ 128/774, 782, 721, 722, 128/748, 903, 675, 680, 681, 687, 689, 694, 733, 775, 776, 777, 778, 779, 780, 781

[56] References Cited

U.S. PATENT DOCUMENTS

| 2,083,335 | 6/1937 | Loudon | 128/721 |
| 2,241,190 | 5/1941 | Fenning | 128/722 |
| 2,812,427 | 11/1957 | Magondeaux | 128/903 |
| 3,087,117 | 4/1963 | Mitchell | 128/903 |
| 3,195,535 | 7/1965 | Westermann | 128/903 |
| 3,603,881 | 9/1971 | Thornton | 128/903 |

Primary Examiner—William E. Kamm
Attorney, Agent, or Firm—Bernard Malina

[57] ABSTRACT

In a device for measuring motion of living body organs, an essential part which defines the oscillation frequency of the oscillator circuit of the device for measuring same comprises an electro-mechanical oscillator of a quartz resonator and impedance elements as coils or capacitors. The motion of organs on a living body surface or in a living body causes impedance changes in an impedance element and therefore, the detector is capable of detecting and measuring living body organ motion through a change in frequency.

9 Claims, 9 Drawing Figures

DEVICE FOR MEASURING MOTION OF LIVING BODY ORGANS

BACKGROUND OF THE INVENTION

This invention relates to a device for measuring motion of living body organs, such as the heart, and more particularly relates to an improvement of stability and accuracy of measurement of a displacement cardiograph which measures motion of the heart on the body's surface without the use of electrodes.

It is a well-known fact that the oscillation coil of a frequency variable oscillator or detection coil is set on the body's surface and the displacement of the body's surface caused by the motion of the heart is detected as a change of oscillation frequency of the frequency variable oscillator.

Until now, the detector has been composed of a coil 5 and frequency variable oscillator provided with capacitors as shown in FIG. 1 and the oscillating frequency changes when the inductance of coil 5 set on the body's surface changes due to the displacement of the body's surface.

However the frequency of the oscillation circuit composed of a combination of coils and capacitors easily changes due to changes in temperature, moisture or source voltage and consequently, it has been impossible to carry out measurement with repetitive accuracy.

SUMMARY OF THE INVENTION

The main object of the invention is to provide a device for measuring motion of living body organs with repetitive accuracy by means of stabilizing the frequency of the frequency variable oscillator of the device for measuring motion of living body organs more than a hundred times than the conventional devices by means of raising sensitivity.

Another object of the invention is to provide a device for measuring motion of living body organs enabling simple and accurate diagnosis of diseases of living body organs, especially of the heart.

A further object of the invention is to provide a device for measuring motion of living body organs which is widely adaptable for the detection of information of motion of living body organs, not only the heart, as the device is non-penetrative, harmless, continuously usable for a long period of time, easy to operate and without contacting the skin of the patient.

Further objects and features of the invention may become clear from the following detailed description.

DETAILED DESCRIPTION OF THE PREFERRED EMBODIMENTS

Figure 1:
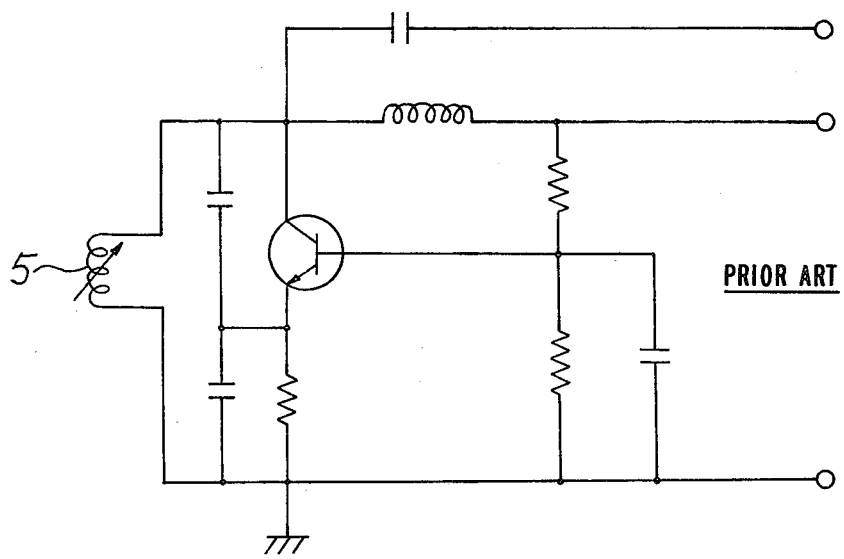
FIG. 1 is a circuit diagram of the conventional LC oscillator.
Figure 2:
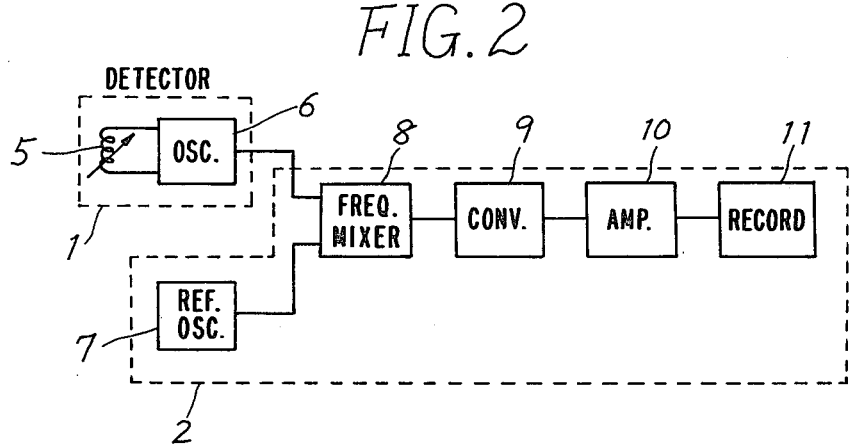
FIG. 2 is a block diagram showing the entire structure of the device in the present invention.

For help of understanding the invention, the entire structure is explained referring to FIG. 2.

FIG. 2 is a block diagram of the structure of this invention which detects the displacement of the body's surface as a result of the change of frequency. In this example, output of oscillation of the detector 1 which is composed of frequency variable oscillator 6 is provided to the frequency mixer 8 simultaneously with the output of oscillation of a reference frequency oscillator 7, the output of the difference between two oscillation frequencies is formed and this output of frequency difference is converted into voltage by the frequency-voltage converter 9 and thereafter, it is amplified by an amplifier 10 and then recorded by a recorder 11.

Figure 3:
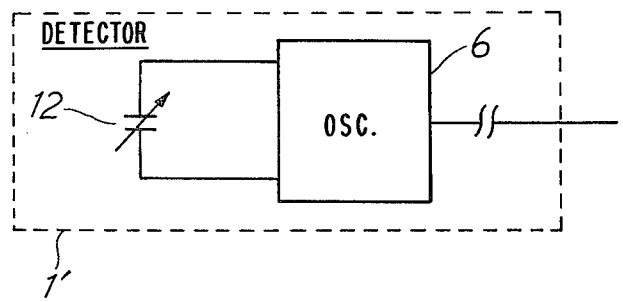
FIG. 3 is a block diagram showing another example of the detector in FIG. 2.

Besides, the reference number 1' in FIG. 3 shows another example of a detector 1 when the detecting capacitor 12 is employed.

Figure 5:
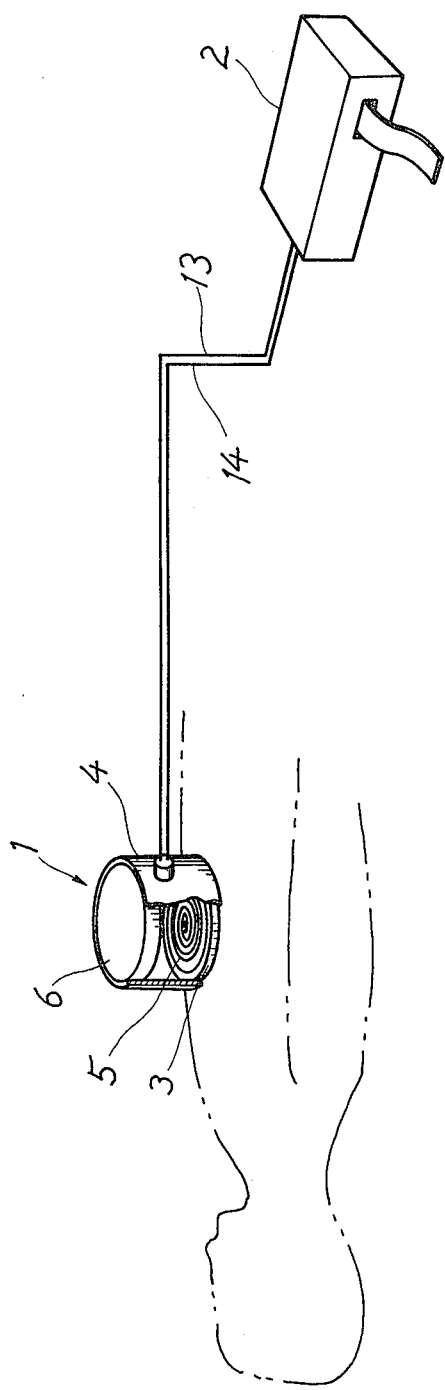
FIG. 5 is an entire structural diagram in which the detector is shown cut partially in a case of employing this invention as a device for measuring motion of the heart.

The detector 1 of this invention is arranged as follows. As shown in FIG. 5, detector coil 5 or detector capacitor 12 is embedded in a plastic disc 3. This plastic disc 3 is fixed on the lower part of a cylinder case 4, the frequency variable oscillator 6 is set on the upper part of the cylinder case 4. Moreover, the source supplying cable 13 and output outlet cable 14 are connected to the frequency variable oscillator, or the source supplying cable 13 and output outlet cable 14 is used in common and connected to the measuring device 2.

By approaching the living body organ with the detector 1, the inductance of the detector coil 5 or capacitance of the detector capacitor 12 in the detector 1 changes. Then, the oscillation frequency of the frequency variable oscillator 6 varies.

As this frequency change is small, after forming the frequency difference between the oscillation frequency of the reference frequency oscillator[7] and that of the frequency variable oscillator 6 by the frequency mixer 8, converting the frequency difference into voltage by frequency-voltage converter 9, and then amplifying the voltage, measuring is simple in spite that the change of inductance or capacitance is very slight. But there is a problem in the frequency stability of the frequency variable oscillator 6. It is very difficult to accurately measure with a conventional LC oscillator.

Figure 4:
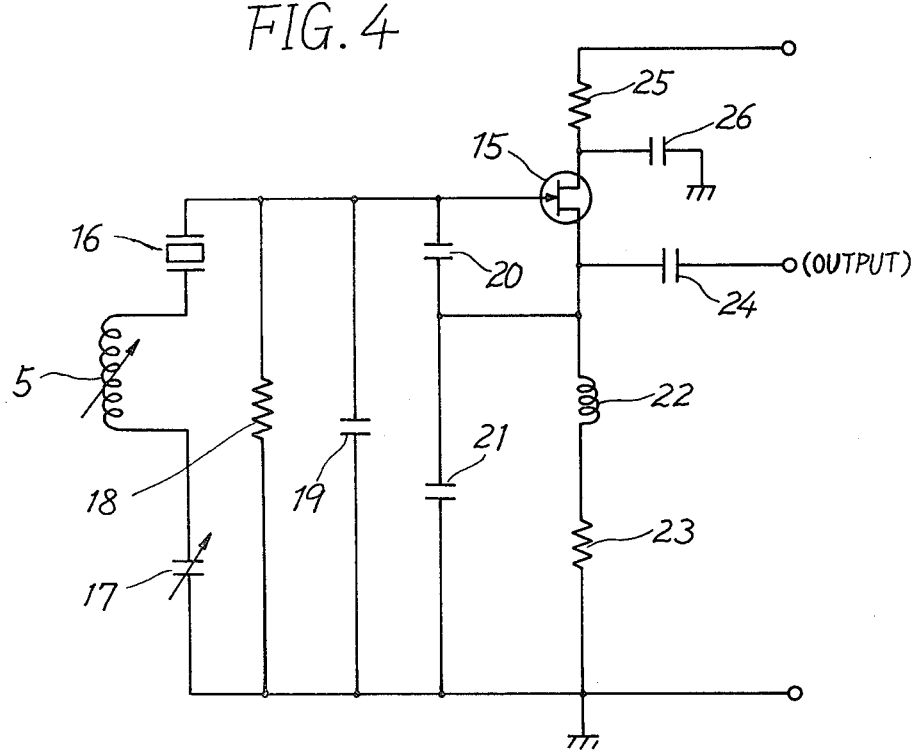
FIG. 4 is a circuit diagram of the oscillation circuit of this invention.

FIG. 4 shows an example of an oscillator circuit of the frequency variable oscillator 6 of this invention which comprises a quartz resonator 16, coil 5 and variable capacitor 17, which are connected in series with the gate electrode of FET(or transistor) 15, with other parts(gate resistor 18, capacitor 19, capacitor between gate and source 20, capacitor between source and drain 21, high frequency choke 22, source resistor 23, output coupling capacitor 24, drain resistor 25, bypass capacitor 26). Moreover, anyone of coil 5, high frequency choke 22 or capacitors 17, 19, 20, 21, 24, 26 may work as a detecting element when close to the body's surface.

Coil 5 of an adequate inductance is externally connected to the quartz resonator 16 in this oscillator circuit and by varying the value of a part of the elements of the oscillator, it is simple to vary the oscillating frequency of the quartz resonator 16 widely and also the circuit keeps the intrinsic stability of the quartz resonator 16.

The value of change of the oscillating frequency is 10–100 times greater than the value of frequency change caused by the variable capacitor 17 without coil 5.

By applying the device for measuring motion of a living body organ, detection with high sensitivity toward the living body organ approaching the detector coil 5 or detector capacitor 12 can be carried out.

The device may work without the variable capacitor 17 on general principles, but frequency can be adjustable by the variable capacitor 17 when the detector is not near the living body organs.

Figure 6:
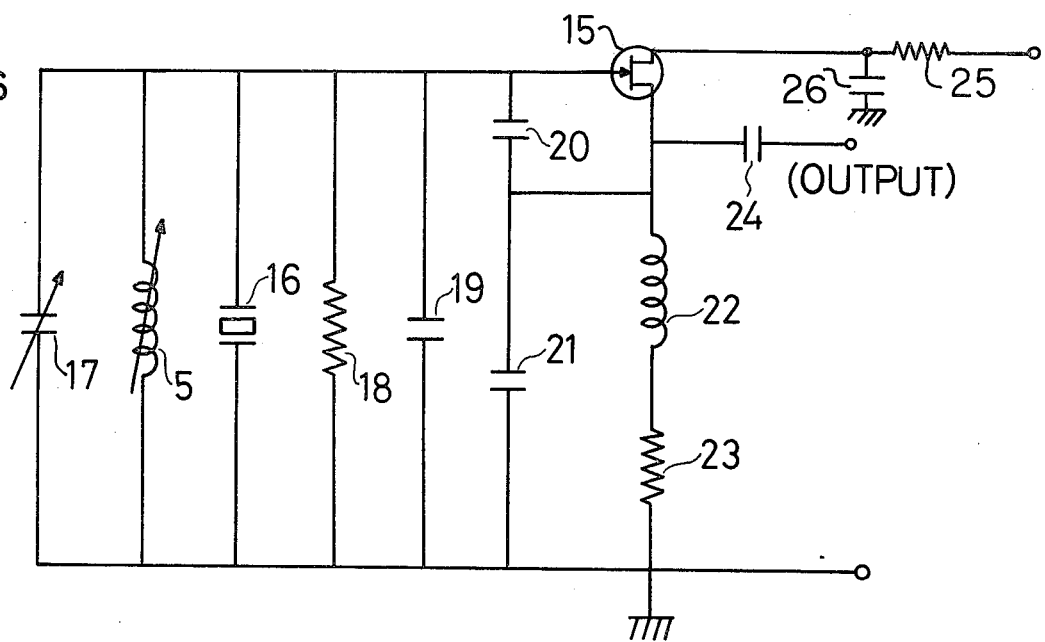
FIG. 6 is a schematic circuit diagram of an oscillator circuit in accordance with the present invention in which the quartz resonator, detector coil and variable capacitor are in parallel arrangement.
Figure 7:
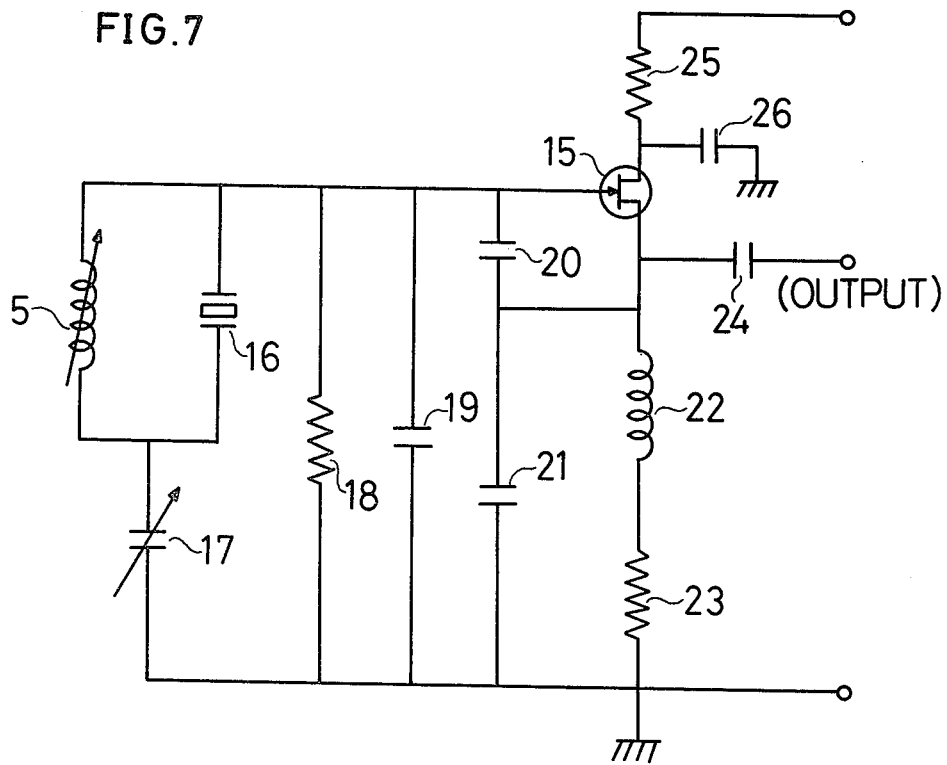
FIG. 7 is a schematic circuit diagram of an oscillator circuit in accordance with the present invention in which the quartz resonator and detector coil are in parallel arrangement and said arrangement is in series with the variable capacitor.
Figure 8:
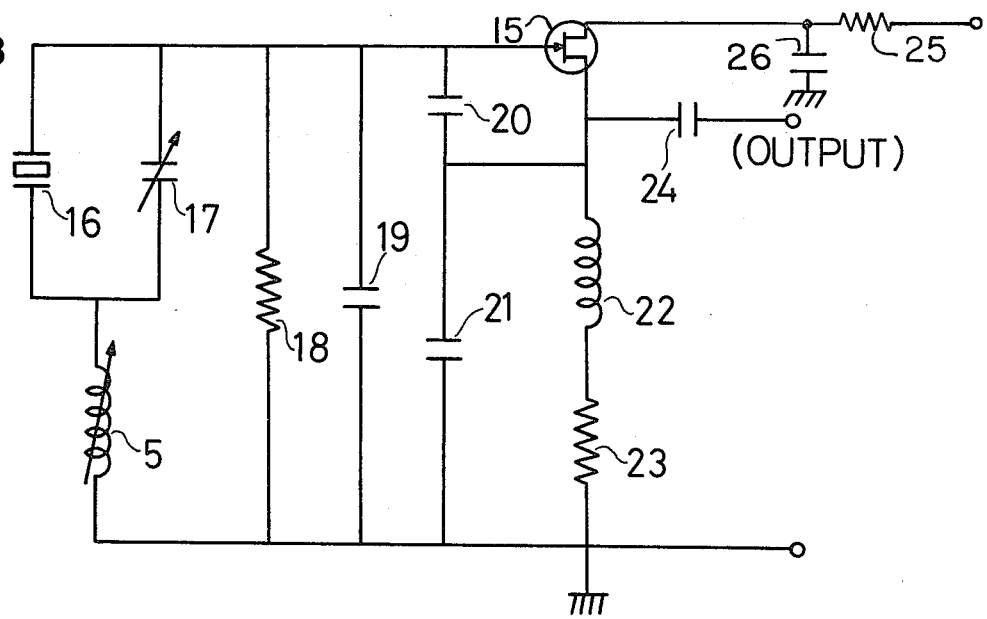
FIG. 8 is a schematic circuit diagram of an oscillator circuit in accordance with the present invention in which the quartz resonator and variable capacitor are in parallel arrangement and said arrangement is in series with the detector coil.
Figure 9:
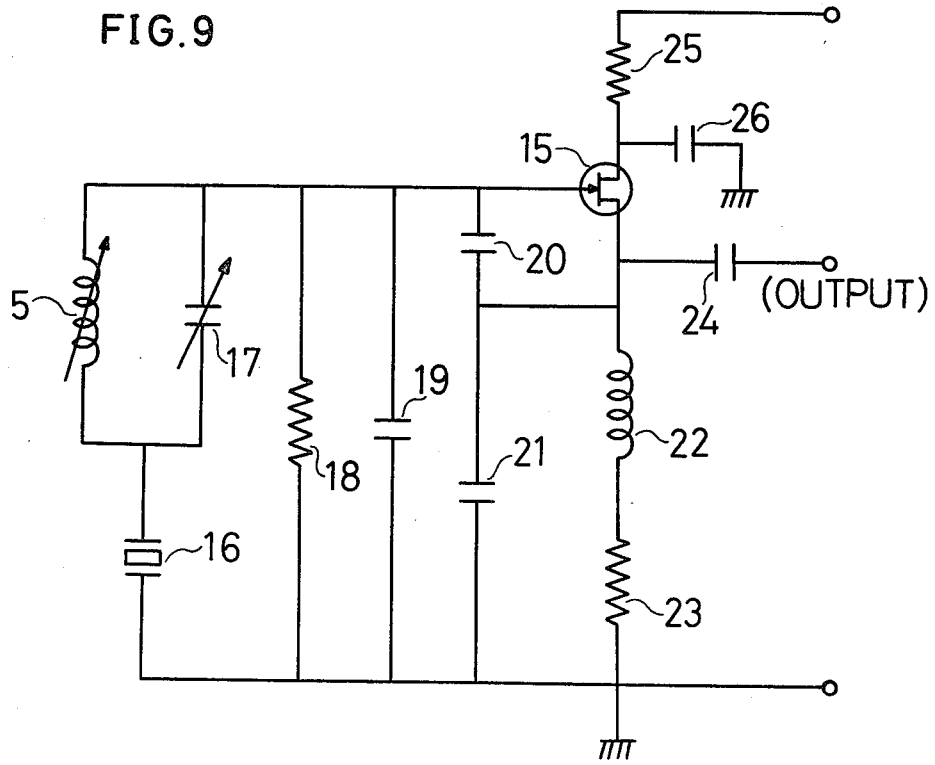
FIG. 9 is a schematic circuit diagram of an oscillator circuit in accordance with the present invention in which the detector coil and variable capacitor are in parallel arrangement and said arrangement is in series with the quartz resonator.

The optimum value of coil 5 is different according to the oscillation frequency. The value to the extent of several tens in $\mu H$ may be needed in some cases, but in such cases, one part of the coil 5 can be used as the detector coil, another part may be set near the quartz resonator 16 as the fixed coil and when the detector capacitor 12 is employed, one part of the necessary capacitance can be used as a detector capacitor and another part may be set near the quartz resonator 16 as a fixed capacitor. According to the principle of duality, it also works when the quartz resonator 16, detector coil 5, variable capacitor 17 are connected in parallel as shown in FIG. 6. Moreover, two of these elements, that is, the quartz resonator 16, coil 5, variable capacitor 17 are connected in parallel, while the remaining element is connected in series with the parallelly-connected elements, or two of them are connected in series and the rest in parallel with same as shown in FIGS. 7–9. It works equally either way.

This invention is so designed as to afford the stable oscillator by utilizing a quartz resonator 16. When the oscillation frequency is set at an optimum value, the detector coil 5 or detector capacitor 12 is only applied to the chest of the patient and the condition of heart motion can be recorded accurately on the recorder 11. Moreover, the recording graph is always stable and further sensitive detection can be achieved.

The invention consists of the construction hereinbefore fully described, illustrated in the accompanying drawings and set forth in the claims hereto appended, it being understood that various changes in the operation, proportion and minor detailes of construction, within the scope of the claims, may be changed without departing from the spirit of the invention or sacrificing any of the advantages thereof.

What is claimed is:

1. A device for measuring motion of a living body organ comprising: oscillator means including quartz resonator means, two-terminal inductance means for producing an electromagnetic field and capacitor means in series arrangement, said oscillator means being operative to produce an output signal having a frequency in accordance with said resonator means, inductance means and capacitor means respectively, the introduction of said organ into said electromagnetic field causing said field and hence the effective inductance of said two-terminal inductance means to vary in accordance with the proximity of said organ to said inductance means, whereby said effective inductance and hence the frequency of said oscillator means output signal varies in accordance with the motion of said organ relative to said inductance means.

2. A device for measuring motion of living body organ as claimed in claim 1 wherein said capacitor means comprises a variable capacitor means.

3. A device for measuring motion of a living body organ as claimed in claim 1 wherein said inductance means comprises manually variable two-terminal inductance means.

4. A device for measuring motion of living body organ comprising: oscillator means including quartz resonator means, two-terminal inductance means for producing an electromagnet field and capacitor means in parallel arrangement respectively; said oscillator means being operative to produce an output signal having a frequency in accordance with said quartz resonator means, inductance means and capacitor means respectively, the introduction of said organ into said electromagnetic field causing said field and hence the effective inductance of said two-terminal inductance means to vary in accordance with the proximity of said organ to said inductance means, whereby said effective inductance and hence the frequency of said oscillator means output signal varies in accordance with the motion of said organ relative to said inductance means.

5. A device for measuring motion of living body organ as claimed in claim 4 wherein said capacitor means comprises variable capacitor means.

6. A device for measuring motion of living body organ as claimed in claim 4, wherein said inductance means comprises manually variable two-terminal inductance means.

7. A device for measuring motion of a living body organ comprising: oscillator means including quartz resonator means, two-terminal inductance means for producing an electromagnetic field and capacitor means, said quartz resonator means and said two-terminal inductance means being in parallel arrangement and said capacitor means being in series with said parallel arrangement; said oscillator means being operative to produce an output signal having a frequency in accordance with said quartz resonator means, inductance means and capacitor means respectively, the introduction of said organ into said electromagnetic field causing said field and hence the effective inductance of said two-terminal inductance means to vary in accordance with the proximity of said organ to said inductance means, whereby said effective inductance and hence the frequency of said oscillator means output signal varies in accordance with the motion of said organ relative to said inductance means.

8. A device for measuring motion of a living body organ comprising: oscillator means including quartz resonator means, two-terminal inductance means for producing an electromagnetic field and capacitor means, said quartz resonator and said capacitor means being in parallel arrangement with each other and said two-terminal inductance means being in series with said parallel arrangement; said oscillator means being operative to produce an output signal having a frequency in accordance with said quartz resonator means, inductance means and capacitor means respectively, the introduction of said organ into said electromagnetic field causing said field and hence the effective inductance of said two-terminal inductance means to vary in accordance with the proximity of said organ to said inductance means, whereby said effective inductance and hence the frequency of said oscillator means output signal varies in accordance with the motion of said organ relative to said inductance means.

9. A device for measuring motion of a living body organ comprising: oscillator means including quartz resonator means, two-terminal inductance means for producing an electromagnetic field and capacitor means, said two-terminal inductance means and said capacitor means being in parallel arrangement with each other and said quartz resonator being in series with said parallel arrangement, said oscillator means being operative to produce an output signal having a frequency in accordance with said quartz resonator means, inductance means and capacitor means respectively, the introduction of said organ into said electromagnetic field causing said field and hence the effective inductance of said two-terminal inductance means to vary in accordance with the proximity of said organ to said inductance means, whereby said effective inductance and hence the frequency of said oscillator means output signal varies in accordance with the motion of said organ relative to said inductance means.

* * * * *